United States Patent
Nierth

(10) Patent No.: US 10,995,104 B2
(45) Date of Patent: May 4, 2021

(54) CATALYSTS FOR REVERSING FORMALDEHYDE ADDUCTS AND CROSSLINKS

(71) Applicant: Roche Molecular Systems, Inc., Pleasanton, CA (US)

(72) Inventor: Alexander Nierth, Dublin, CA (US)

(73) Assignee: Roche Molecular System, Inc., Pleasanton, CA (US)

( * ) Notice: Subject to any disclaimer, the term of this patent is extended or adjusted under 35 U.S.C. 154(b) by 249 days.

(21) Appl. No.: 15/991,087

(22) Filed: May 29, 2018

(65) Prior Publication Data

US 2018/0370992 A1    Dec. 27, 2018

Related U.S. Application Data

(60) Provisional application No. 62/512,324, filed on May 30, 2017.

(51) Int. Cl.
| | |
|---|---|
| C12Q 1/68 | (2018.01) |
| C07F 5/02 | (2006.01) |
| C12Q 1/6844 | (2018.01) |
| C12Q 1/6806 | (2018.01) |
| G01N 1/30 | (2006.01) |

(52) U.S. Cl.
CPC ............ *C07F 5/025* (2013.01); *C12Q 1/6806* (2013.01); *C12Q 1/6844* (2013.01); *C12Q 2523/101* (2013.01); *G01N 1/30* (2013.01)

(58) Field of Classification Search
CPC ... C07F 5/025; C07F 9/40; C07F 9/94; C12Q 1/6806; C12Q 1/6844; G01N 1/30
See application file for complete search history.

(56) References Cited

U.S. PATENT DOCUMENTS

| | | | |
|---|---|---|---|
| 8,652,775 B2 | 2/2014 | Will et al. | |
| 9,400,235 B2 | 7/2016 | Will et al. | |

FOREIGN PATENT DOCUMENTS

WO    2016044313 A1    3/2016

OTHER PUBLICATIONS

International Search Report and Written Opinion dated Jul. 13, 2018 in corresponding PCT/EP2018/064161 filed on May 30, 2018, pp. 1-10.
Wassef, M., A Cytochemical Study of Interchromatin Granules, Journal of Ultrastructure Research, Oct. 1, 1979, pp. 121-133, vol. 69, No. 1.
Adamczyk-Wozniak, A. et al., "Benzoxaboroles—Old compounds with new applications", Journal of Organometallic Chemistry, 2009, 694 (22), p. 3533-3541.
Candeias, N.R. et al., "Boronic acids and esters in the Petasis-bornono Mannich multicomponent reaction", Chemical Reviews, 2010, 110 (10), p. 6169-6193.
Cong, X. et al., "Chemoselective deprotection of cyclic N, O-aminals using catalytic bismuth(III) bromide in acetonitrile", Journal of Organic Chemistry, 2005, 70 (11), p. 4514-4516.
Connon, S.J. "Chiral phosphoric acids: powerful organocatalysts for asymmetric addition reactions to imines", Angewandte Chemie (Int. Ed.), 2006, 45 (24), p. 3909-3912.
Karmakar, S. et al., "Organocatalytic removal of formaldehyde adducts from RNA and DNA bases", Nature Chemistry, 2015, 7 (9), p. 752-758.
Rashidian, M., et al., "A highly efficient catalyst for oxime ligation and hydrazone-oxime exhange suitable for bioconjugation", Bioconjugate Chemistry, 2013, 24 (3), p. 333-342.
Sutherland, B.W. et al., "Utility of formaldehyde cross-linking and mass spectrometry in the study of protein-protein interactions",Journal of Mass Spectrometry, 2008, 43 (6), p. 699-715.
Zhang, Y.-K. et al., "Synthesis and structure-activity relationships of novel benzoxaboroles as a new calss of antimalarial agents", Bioorganic & Medicinal Chemistry Letters, 2011, 21 (2), p. 644-651.

*Primary Examiner* — Jezia Riley
(74) *Attorney, Agent, or Firm* — David J. Chang

(57) ABSTRACT

Catalysts act to release formaldehyde cross-linking that occurs in biological samples. Thus, contacting catalysts to formaldehyde fixed samples is a useful way to render biological components of the samples, including nucleic acids or proteins, more accessible to detection and characterization.

20 Claims, 3 Drawing Sheets

CATALYSTS FOR REVERSING FORMALDEHYDE ADDUCTS AND CROSSLINKS

CROSS REFERENCE TO RELATED APPLICATIONS

This application claims the benefit of priority of U.S. Provisional Patent Application Ser. No. 62/512,324, filed May 30, 2017, which is incorporated herein by reference in its entirety.

BACKGROUND OF THE INVENTION

For over a hundred years, pathologists have routinely preserved biological samples such as tissue samples by fixing them with formaldehyde. While formaldehyde treatment preserves the cellular features of the tissue, formaldehyde treatment also results in chemical cross-linking that renders many of the biological components of the sample poorly accessible or inaccessible to detection, quantification and characterization. Formaldehyde preserves or fixes tissue or cells by cross-linking primary amine groups in proteins with other nearby nitrogen atoms in protein or DNA through a —$CH_2$— linkage. Thus, for example, while the polymerase chain reaction (PCR) is useful to detect and quantify nucleic acids in biological samples, PCR is generally poorly or not effective in analyzing nucleic acids in formaldehyde cross-linked samples, especially where quantitative results are desired.

Cross-linking of nucleic acids to cellular components by the action of formaldehyde thus presents challenges to the detection of various cellular components, including detection of nucleic acids and proteins. While some have described ways of improving amplification of nucleic acids from formaldehyde cross-linked samples, the improvements generally involve merely degrading protein in the sample or providing detergents that do not generally change the covalent bonds forming the cross-links. The present invention addresses this and other problems.

BRIEF SUMMARY OF THE INVENTION

The present invention provides methods for analyzing one or more components of a formaldehyde cross-linked biological sample. In some embodiments, the methods comprise contacting the sample with a sufficient amount of a catalyst to release at least a portion of the cross-linked component, thereby improving the accessibility of the one or more components for analysis.

In some embodiments the biological sample is a tissue sample from an animal.

In some embodiments the amount of catalyst is between about 0.2 mM and about 5.0 mM.

In some embodiments the sample and catalyst are heated for a period of at least 10 minutes.

In some embodiments, the methods further comprise detecting the component.

In some embodiments, the catalyst is substantially removed from the sample prior to the detecting step. In some embodiments, the concentration of catalyst is reduced to less than about 0.1 mM prior to the detecting step.

In some embodiments, the detecting step comprises quantifying the component.

In some embodiments, the component is a nucleic acid. In some embodiments, the nucleic acid is DNA. In some embodiments, the component is RNA.

In some embodiments, the methods further comprise detecting the nucleic acid. In some embodiments, the detecting step comprises amplifying the nucleic acid. In some embodiments, the nucleic acid component is contacted to a probe under conditions to allow for formation of the probe and nucleic acid, and detecting the presence of the duplex. In some embodiments, the probe is linked to a solid support. In some embodiments, the amplifying step comprises the polymerase chain reaction.

In some embodiments, the component is protein. In some embodiments, the methods further comprise detecting the protein. In some embodiments, the detecting step comprises mass spectrometry or electrophoresis. In some embodiments, the mass spectrometry comprises matrix-assisted laser desorption/ionization (MALDI).

In some embodiments, the sample is embedded in paraffin prior to the contacting step.

In some embodiments, the catalyst is selected from the group consisting of (2-Amino-5-fluorophenyl) boronic acid, 2-Aminophenyl boronic acid, (2-Amino-5-methylphenyl) boronic acid, 1,3-Dihydro-1-hydroxy-2,1-benzoxaborol-7-amine, 3,4-Dihydro-1-hydroxy-1H-2,1-benzoxaborin-7-amine, (Aminophenylmethyl) phosphonic acid diethyl ester, Bismuth (III) bromide, Bismuth (III), iodide, Bismuth (III) citrate and Bismuth (III) salicylate.

In some embodiments, the portion of the component that is available for analysis is increased at least about two-fold compared to the portion accessible for analysis if the contacting step is not performed. In some embodiments, the portion of the component that is available for analysis is increased at least about ten-fold compared to the portion accessible for analysis if the contacting step is not performed.

In some embodiments, the methods further comprise contacting the sample with a protease to degrade the protein in the sample, thereby rendering the nucleic acids more available for analysis.

The present invention also provides a kit for improving the availability of one or more components of a formaldehyde cross-linked biological sample. In some embodiments, the kit comprises a catalyst; and a protease or a reagent or device for removal of the catalyst from a biological sample, wherein the catalyst is selected from the group consisting of an aminophenyboronic acid, a cyclic boronic acid ester, a phosphonic acid ester, and a bismuth salt.

In some embodiments, the kit comprises a reagent or device for removal of the catalyst from a biological sample. In some embodiments, the device is a column for purification of nucleic acids.

In some embodiments, the kit comprises a protease. In some embodiments, the protease is proteinase K.

In some embodiments, the kit further comprises nucleotides and/or a thermostable polymerase. In some embodiments, the thermostable polymerase is Taq polymerase.

In some embodiments, the catalyst is selected from the group consisting of (2-Amino-5-fluorophenyl) boronic acid, 2-Aminophenyl boronic acid, (2-Amino-5-methylphenyl) boronic acid, 1,3-Dihydro-1-hydroxy-2,1-benzoxaborol-7-amine, 3,4-Dihydro-1-hydroxy-1H-2,1-benzoxaborin-7-amine, (Aminophenylmethyl) phosphonic acid diethyl ester, Bismuth (III) bromide, Bismuth (III), iodide, Bismuth (III) citrate and Bismuth (III) salicylate.

The present invention also provides reaction mixtures. In some embodiments, the reaction mixtures comprise a formaldehyde cross-linked biological sample; and a sufficient amount of a catalyst to release at least a portion of the cross-linked component, wherein the catalyst is selected from the group consisting of an aminophenyboronic acid, a cyclic boronic acid ester, a phosphonic acid ester, and a bismuth salt.

In some embodiments, the amount of catalyst is between 0.2 mM and 5.0 mM. In some embodiments, the catalyst is selected from the group consisting of (2-Amino-5-fluorophenyl) boronic acid, 2-Aminophenyl boronic acid, (2-Amino-5-methylphenyl) boronic acid, 1,3-Dihydro-1-hydroxy-2,1-benzoxaborol-7-amine, 3,4-Dihydro-1-hydroxy-1H-2,1-benzoxaborin-7-amine, (Aminophenylmethyl)phosphonic acid diethyl ester, Bismuth (III) bromide, Bismuth (III), iodide, Bismuth (III) citrate and Bismuth (III) salicylate. In some embodiments, the biological sample is a tissue sample from an animal.

Definitions

A "formaldehyde cross-linked biological sample" refers to a biological sample that has been treated with formaldehyde such that cross-linking is formed between a nitrogen in proteins or nucleic acids to other nitrogen-containing proteins and/or nucleic acids. A biological sample will typically contain cells. The biological sample can be, for example, a tissue sample from an animal, for example, from a human. Many formaldehyde-treated samples are stored by embedding them in paraffin.

As used herein, the term "catalyst" refers to an agent that catalyzes the removal of adducts and/or crosslinks from fixed biomolecules (e.g., aldehyde fixed biomolecules, formaldehyde fixed biomolecules), upon contact with a sample having aldehyde fixed biomolecules (e.g. a FFPE biological sample). A catalyst can be said to remove crosslinks as well as other adducts (e.g. aldehyde fixation relate adducts, formaldehyde fixation related adducts). In some cases, the pKa of the catalyst is in a range of from 2.5 to 9.0. In some embodiments, the catalyst is selected from the compounds in TABLE 1. One of skill in the art will appreciate that other catalysts are useful in the present invention.

The phrase "detecting the component" refers to determining at least the presence or absence of the component and can include further quantification or other characterization of the component or part of the component.

A "component" of a biological sample refers to a class of molecules (e.g., proteins, nucleic acids, etc.) or a specific target such as a specific protein or nucleic acid sequence that one wishes to detect.

As used herein, the term "nucleic acid" refers to polymers of deoxyribonucleotides (containing 2-deoxy-D-ribose) (i.e., DNA), polyribonucleotides (containing D-ribose) (i.e., RNA), and any other N-glycosidic analogs of a purine or pyrimidine base, or modified purine or pyrimidine bases.

The phrase "to release at least a portion of the cross-linked component" refers to altering the covalent bonds forming a cross-linkage between two components (e.g., a nucleic acid and a protein) of the biological sample such that the two components are no longer linked by a covalent bond. The phrase encompasses, but is not limited to, a complete reversal of the cross-linking process.

The phrase "accessibility for analysis" as used herein refers to the ability of a detection method to determine the presence or absence and/or quantity of a particular target molecule. For example, numerous detection methods are at least partly inhibited from detecting protein or nucleic acids in a formaldehyde cross-linked biological sample and thus certain cross-linked components are not "accessible" for detection. Once cross-linking is released by treatment with a catalyst, an increased amount (e.g., at least about 10% more and typically at least about 2-fold more, or sometimes about at least 10 or 100-fold more) of the component can be detected and quantified.

DETAILED DESCRIPTION OF THE INVENTION

I. Introduction

Figure 1:
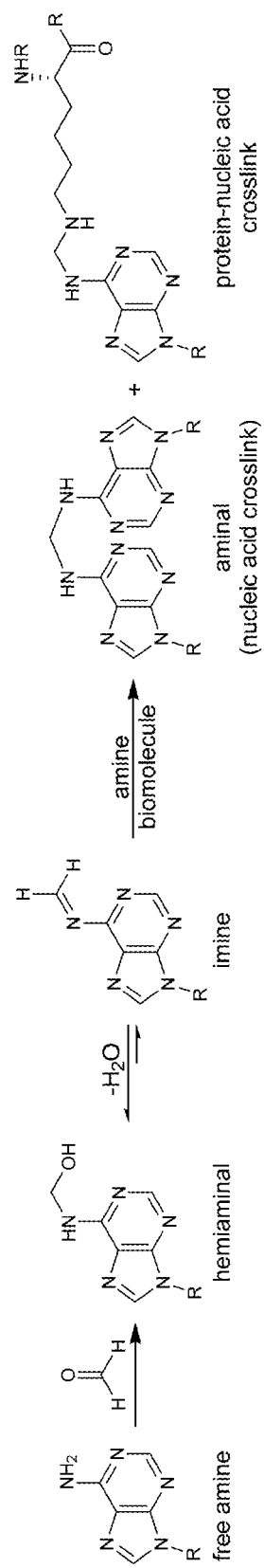
FIG. 1 illustrates the reaction of formaldehyde to convert a free amine to its hemiaminal adduct and imine intermediate which can further react with other amines to form aminal crosslinks.

As shown in FIG. 1, formaldehyde readily reacts with the nitrogen nucleophiles of nucleic acids (adenine, guanine) and proteins (α-amino groups in the protein backbone or ε-amino group of lysine). The hemiaminal adducts form imine intermediates, which further react with other amines, thereby creating intra- and intermolecular aminal crosslinks. As a result of the cross-linking, various biological components in formaldehyde-fixed samples are not accessible to modern detection methods. The present invention provides methods of reversing the cross-linking, thereby rendering more of the biological components accessible for detection.

Reversal of the cross-linking in formaldehyde-treated samples is achieved by contacting the samples with a sufficient amount of a catalyst to release the cross-linking reaction. Examples of cross-linking is depicted in FIG. 1.

Once cross-linked samples are contacted with a catalyst, cross-linking of nucleic acids and proteins is reduced or eliminated, thereby allowing for improved detection of these components.

II. Methods for Rendering Cross-Linked Components More Accessible

The present invention provides for methods of rendering formaldehyde cross-linked components of a biological sample more accessible for detection by contacting the sample with a catalyst. The quantity of catalyst used to render the components more accessible can vary and will depend in part on the specific catalyst used, the component to be detected, and the detection method to be used as different detection methods have different sensitivities and so may require more or less of the component to be accessible.

Ideally, the amount of a component rendered accessible to a particular detection method will be the entire amount of the component in the sample. However, generally, the amount of component rendered accessible for detection will be less than the entire quantity of the component in the sample. In some embodiments of the invention, a sufficient amount of catalyst is used under conditions to render at least about two times the amount of the component accessible for detection as would be accessible (using the same detection method) if the sample was not treated with the catalyst. In some embodiments, a sufficient amount of catalyst is used under conditions to render at least about 5, 10, 20, 100 times the amount of the component accessible for detection as would be accessible (using the same detection method) if the sample was not treated with the catalyst. In some embodiments, the concentration of catalyst used to release the cross-linking of the sample is between about 0.2 mM and about 5.0 mM (or more).

Those of ordinary skill in the art will appreciate that the conditions (e.g., time and temperature) in which the sample and catalyst are combined will affect the ability and amount of cross-linkage reversal. Catalyst treatment is effective at ambient (e.g., between 20-40 or 50° C.) temperature and thus does not necessarily require a heating step to release cross-linkages. This can be particularly useful when detecting components that are relatively labile, such as RNA. Nevertheless, higher temperature (e.g., 80-100° C., 90-100° C., 90-99° C., etc.) may further improve the accessibility of nucleic acids or proteins for detection.

Moreover, the amount of time the catalyst is incubated with the sample will affect the amount of the components rendered accessible for detection. For example, the samples can be incubated with the catalyst for at least about 5, 10, 20, 30, 60, 120 minutes or more. While a longer time of incubation may increase the amount of component that is released from cross-linking, this may need to be balanced with how labile a particular component may be. For example, it may be desirable to use a shorter incubation time when a labile component such as RNA is to be detected. On the other hand, a less labile component, such as protein or DNA, can be exposed to a longer incubation without harming the component.

It will be recognized that different catalysts can be used to release cross-linking. Without intending to limit the scope of the present invention, the selected catalyst will generally be capable of releasing the components from the formaldehyde-induced cross linkages and reverting the components (e.g., nucleic acids and/or protein) to substantially the same component as existed prior to the formaldehyde cross-linking. The cross-linking reaction is reversible process that proceeds by reaction of formaldehyde and a first amine to form a hemiaminal, followed by dehydration to afford an imine. The imine reacts with a second amine to afford the product aminal. The process reverts to the starting materials by reaction of the imine with water instead of a second amine. It is believed the catalyst of the present invention releases the components from the formaldehyde-induced cross linkages by acting as a competitive reactant in the formation of the imine and the aminal. When the cross-linkages release as part of the equilibrium process, the imine intermediate and the formaldehyde react with the catalyst, thereby releasing the components from the formaldehyde-induced cross linkages.

Catalysts used to practice the methods of the invention may include aminophenylbornoic acids, cyclic boronic acid esters (benzoxaborines), phosphonic acid esters, and bismuth salts and complexes. These catalysts accelerate the cleavage of formaldeyde adducts and crosslinks at mild reaction conditions, thereby increasing the quality of nucleic acids from FFPET samples. Specific embodiments of catalysts useful for the present invention are selected from the compounds shown in TABLE 1.

TABLE 1

| No. | Compound name | Chemical formula | Descriptor | CAS number | Molecular weight [g/mol] |
|---|---|---|---|---|---|
| Boronic acids and esters | | | | | |
| 1 | (2-Amino-5-fluorophenyl)boronic acid | 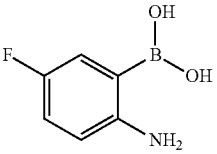 | 2A5FPB | 1040400-87-0 | 154.93 |
| 2 | 2-Aminophenylboronic acid | 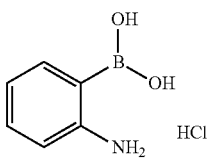 | 2APB | 5570-18-3 863753-30-4 (HCl) | 173.40 |
| 3 | (2-Amino-5-methyl phenyl)boronic acid | 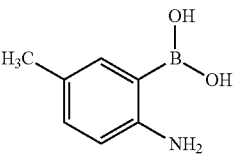 | 2A5MPB | 948592-72-1 | 150.97 |
| 4 | 1,3-Dihydro-1-hydroxy-2,1-benzoxaborol-7-amine | 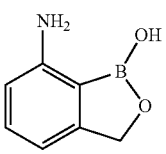 | BOB7A | 947165-27-7 | 148.96 |

TABLE 1-continued

| No. | Compound name | Chemical formula | Descriptor | CAS number | Molecular weight [g/mol] |
|---|---|---|---|---|---|
| 5 | 3,4-Dihydro-1-hydroxy-1H-2,1-benzoxaborin-7-amine | | BOBN | N/A | 162.98 |
| Phosphonic acid esters | | | | | |
| 6 | (Aminophenylmethyl) phosphonic acid diethyl ester | | APMPDE | 16814-08-7 16656-50-1 (HCl) | 279.70 |
| Bismuth salts and complexes | | | | | |
| 7 | Bismuth(III) bromide | BIBr$_3$ | BIBr$_3$ | 7787-58-8 | 448.69 |
| 8 | Bismuth(III) iodide | BII$_3$ | BII$_3$ | 7787-64-6 | 589.69 |
| 9 | Bismuth(III) citrate | BI(citrate) | BI(citrate) | 813-93-4 | 398.08 |
| 10 | Bismuth(III) sallcylate | | BI(sal)OH | 14882-18-9 | 362.09 |

The key properties for the catalysts described in the present invention are: Catalysis of aminal cleavage (i.e. the reverse reaction or "de-crosslinking"), no detrimental effects on nucleic acids and other biomolecules, sufficient water solubility, compatibility with nucleic acid purification protocols, amenability to automation, and safe handling (i.e. non-toxicity). Furthermore, the catalysts should operate at reaction conditions that minimize nucleic acid, protein or biomolecule impairment (e.g. pH range of 4.5-8.0, temperature range of 25° C.-60° C., time period of at least 10 minutes and less than 60 minutes). The addition of a catalyst that allows the extraction of nucleic acids and other biomolecules to be performed at mild reaction conditions is expected to significantly improve the quality of the extracted material. As such, these compounds may find broad application in manual and automated nucleic acid and protein extraction and recovery protocols.

Any type of formaldehyde cross-linked biological sample can be used according to the methods of the invention. Generally, the tissue samples will be derived from animal tissues. In some embodiments, the samples will be embedded in paraffin. For example, the samples can be formalin fixed paraffin embedded tissue (FFPET). In some embodiments, the samples have been obtained from an animal (e.g., a human) and then stored in a formaldehyde-containing solution to stabilize the sample prior to analysis, thereby cross-linking the nucleic acids and/or protein in the sample. For example, a cervical or other gynecological swab (e.g., for detection of sexually transmitted disease) can be stored in a solution containing formaldehyde, thereby cross-linking the nucleic acids and/or protein in the sample. The cross-linking can be subsequently reversed using a catalyst according to the methods of the invention.

To further render the sample components accessible to detection, additional purification or other steps may be included in the methods of the invention. For example, if a nucleic acid component of the sample is to be detected, it can be helpful to treat the sample (e.g., before or following catalyst treatment) with a protease, or otherwise degrade the protein in the sample. An exemplary protease is proteinase K, though it will be appreciated that various other proteases could be substituted.

Also depending on the detection method to be used subsequently, it can be desirable to remove or at least reduce the amount of catalyst associated with the sample before detecting a component. For example, the inventors have found it helpful to purify the nucleic acids in the sample from other components of the sample as well as from the catalyst by using a reagent or device such as a spin column to purify nucleic acids from other parts of the sample. An exemplary device is a silica-based spin column with affinity for nucleic acids (such as the Qiaquick™ spin column from Qiagen, Valencia, Calif.), though of course other purification methods may also be used to remove the catalyst.

II. Detection of Components of Cross-Linked Biological Samples

Any detection method may be used in combination with the catalyst treatment described above to detect a component of the previously cross-linked sample. As described in further detail below, exemplary components of the sample for which cross-linking interferes with detection include nucleic acids and proteins. Detection of components can involve simply determining the presence or absence of a particular component or part (e.g., a particular protein or nucleic acid sequence) of the component. Alternatively, detection can involve quantification of the component and/or characterization of the component. Characterization can include, for instance, peptide or nucleic acid sequencing and/or determination of post-transcriptional or translational modifications, including, e.g., glycosylation, phosphorylation, etc.

A. Nucleic Acids

Numerous methods for detecting nucleic acids are known in the art. DNA or RNA (including mRNA, rRNA, etc.), or both can be detected. Detection can include quantification of a particular sequence or RNA, and/or characterization of a nucleic acid, for example, by nucleotide sequencing or sequence-specific hybridization techniques (e.g., such as those used to detect single nucleotide polymorphisms (SNPs) and the like).

As many paraffin-embedded, formaldehyde-treated samples are relatively small, it is often desirable to use amplification methods to amplify a particular nucleic acid to assist in detection of nucleic acids. Any type of amplification method may be used, including exponential amplification methods, linear amplifications, thermocycling or isothermal methods, etc. Suitable amplification methods include, but are not limited to, the polymerase chain reaction (PCR) (*Principles and Applications for DNA Amplification* (ed. H. A. Erlich, Freeman Press, NY, N.Y., 1992); *PCR Protocols: A Guide to Methods and Applications* (eds. Innis, et al., Academic Press, San Diego, Calif., 1990); Current Protocols in Molecular Biology, Ausubel, 1994-1999, including supplemental updates through April 2004; Sambrook & Russell, Molecular Cloning, A Laboratory Manual (3rd Ed, 2001)), the ligase chain reaction (LCR) (U.S. Pat. Nos. 5,185,243, 5,679,524 and 5,573,907; EP 0 320 308 B1; WO 90/01069; WO 89/12696; and WO 89/09835), cycling probe technology (U.S. Pat. Nos. 5,011,769, 5,403,711, 5,660,988, and 4,876,187, and PCT published applications WO 95/05480, WO 95/1416, and WO 95/00667), Invader™ technology (U.S. Pat. Nos. 5,846,717; 5,614,402; 5,719,028; 5,541,311; and 5,843,669), Q-Beta replicase technology (U.S. Pat. No. 4,786,600), NASBA (U.S. Pat. No. 5,409,818; EP-0 329 822), TMA (U.S. Pat. Nos. 5,399,491, 5,888,779, 5,705,365, 5,710,029), SDA (U.S. Pat. Nos. 5,455,166 and 5,130,238). Numerous different polymerases can be used in the amplifications. A representative thermostable enzyme isolated from *Thermus aquaticus* (Taq) is described in U.S. Pat. No. 4,889,818 and a method for using it in conventional PCR is described in Saiki et al., 1988, *Science* 239:487-91. Another representative thermostable enzyme includes *Thermus* species Z05 DNA polymerase. See, e.g., U.S. Pat. No. 5,674,738. Optionally, real-time PCR or other quantitative amplification techniques can be used to quantify a particular nucleic acid sequence. Methods of quantitative amplification are disclosed in, e.g., U.S. Pat. Nos. 6,180,349; 6,033,854; and 5,972,602, as well as in, e.g., Gibson et al., *Genome Research* 6:995-1001 (1996); DeGraves, et al., *Biotechniques* 34(1):106-10, 112-5 (2003); Deiman B, et al., *Mol Biotechnol.* 20(2):163-79 (2002). This can be particularly useful following reverse transcription reactions (RT-PCR) so that RNA levels for one or more gene can be measured within a sample. RT-PCR methods are well known to those of skill (see, e.g., *Current Protocols in Molecular Biology* (Ausubel et al., eds., 2002)) and are readily adapted for quantitative amplification methods.

Other methods can also be used to detect nucleic acids. For example, nucleic acids can be isolated from a sample and hybridized to a probe. In some instances, the probe will be linked to a solid support (e.g., a microarray).

B. Proteins

Protein components of a sample can also be detected following treatment with a catalyst. Any of a variety of protein detection and characterization methods may be employed according to the method of the present invention.

An exemplary protein detection method is mass spectrometry. Exemplary mass spectrometry methods include, but are not limited to, electrospray ionization and matrix-assisted laser desorption/ionization (MALDI), including MALDI time of flight (MALDI-TOF) methods. See, e.g., Karas, M.; Hillencamp, F. Anal. Chem. 60:2301 (1988); Beavis, R. C. Org. Mass Spec. 27:653 (1992); Creel, H. S. *Trends Poly. Sci.* 1(11):336 (1993).

One alternative to detection with mass spectrometry is use of electrophoresis to separate and subsequently detect proteins of interest. Electrophoresis methods include two-dimensional electrophoresis methods. The methods can optionally include subsequent western blot detection of proteins with antibodies.

Other options include immuno-detection of proteins. Various ELISA and other formats for immuno-detection of proteins are well known.

III. Kits

The present invention also provides kits useful for employing the above-described methods of the invention. As such, the kits can comprise one or more of the reagents described herein. Optionally, the kits can include written (paper) or electronic instructions for their use.

In some embodiments, the kits of the invention will include a catalyst with at least one additional reagent for detection or improving detection of a nucleic acid or protein. For example, in some embodiments, the kits comprise a catalyst and a protease (including but not limited to proteinase K) for degrading protein and rendering nucleic acids even more accessible to detection. Other reagents for detection or improving detection of a nucleic acid or protein include, e.g., reagents useful for amplifications. For example, a typical polymerase chain reaction can include, without limitation, as reagents upstream and downstream primers, at least one template, deoxyribonucleoside triphosphates (including dATP, dCTP, dGTP, TTP, dUTP), a polymerase enzyme, buffers, metal cations and salts. A kit for an RT-PCR reaction can also include a reverse transcriptase and/or primers. For quantitative (e.g., "real-time") amplification, one or more polynucleotide probes are employed to hybridize to the desired target. The probes are typically labeled with a detectable label, e.g., a fluorescent label. An exemplary probe is a Taqman™ probe, though it will be appreciated that other types of probes can be used to monitor a target in a quantitative amplification reaction. A nucleic acid sequence-based amplification (NASBA) reaction can include primers, reverse transcriptase, RNase H, and a DNA polymerase. A transcription-mediated amplification (TMA) reaction can include primers, reverse transcriptase, and an RNA polymerase. A strand displacement amplification (SDA) reaction can include a modified nucleotide and a restriction endonuclease. Certain amplification reactions can also include deoxyUridine N-Glycosylase (UNG) as an ancillary amplification reagent (e.g., Amperase®, Roche Molecular Sciences, Alameda, Calif.) (see, Kleiboeker, *Virol J* (2005) 11:29).

Other reagents for detection or improving detection of a nucleic acid or protein include, e.g., reagents or devices for purifying proteins or nucleic acids, for example as described herein.

IV. Reaction Mixtures

The present invention also provides reaction mixtures. An exemplary reaction mixture will comprise a formaldehyde-fixed sample, optionally including paraffin, and a catalyst as described herein. The reaction mixtures can include the concentrations of catalyst that are described above. Further, the reaction mixtures are optionally at the temperatures recited above. Reaction mixtures can optionally further include a protease (e.g., proteinase K).

EXAMPLE

Example 1

This example illustrates the preparation and analysis of formaldehyde adducts of mononucleotides.

Materials and Reagents.

Deoxyadenosine monophosphate (dAMP), lithium perchlorate, and all organic catalysts were purchased from Sigma-Aldrich or VWR. Methanol-free 10% formaldehyde, EM grade was purchased from Thermo Fisher Scientific. Solvents and reagents were purchased from Sigma-Aldrich or VWR. The names, CAS numbers and Molecular Weights of the compounds (catalysts) are as follows:

Compound 1: (2-Amino-5-fluorophenyl)boronic acid; CAS number 1040400-87-00; Molecular Weight 154.93.
Compound 2: 2-Aminophenylboronic acid; CAS number 5570-18-3/863753-30-4 (HCl); Molecular Weight 173.40.
Compound 3: (2-Amino-5-methylphenyl)boronic acid; CAS number 948592-72-1; Molecular Weight 150.97.
Compound 4: 1,3-Dihydro-1-hydroxy-2,1-benzoxaborol-7-amine; CAS number 947165-27-7, Molecular Weight 148.96.
Compound 5: 3,4-Dihydro-1-hydroxy-1H-2,1-benzoxaborin-7-amine; CAS number N/A; Molecular Weight 162.98.
Compound 6: (Aminophenylmethyl)phosphonic acid diethyl ester; CAS number 16814-08-7/16656-50-1(HCl); Molecular Weight 279.70.
Compound 7: Bismuth (III) bromide; CAS number 7787-58-8; Molecular Weight 448.69
Compound 8: Bismuth (III) iodide; CAS number 7787-64-6; Molecular Weight 589.69
Compound 9: Bismuth (III) citrate; CAS number 813-93-4; Molecular Weight 398.08
Compound 10: Bismuth (III) salicylate; CAS number 14882-18-9; Molecular Weight 362.09.

Characterization.

Formation of $N^6$-hydroxymethyl-dAMP was confirmed by ESI-MS, which was in agreement with the literature. The high-resolution mass of N6-hydroxymethyl-dAMP was found to be 362.0852 ([M+H]$^+$, $C_{11}H_{17}N_5O_7P$, Calc. 362.0860).

Synthesis of Methylene-Bis-Deoxyadenosine-5'-Monophosphate (Dimer).

0.06 M solution of dAMP (in deionized water) and 0.3 M solution of 10% formaldehyde (methanol free) in 0.2 M sodium acetate buffer (pH 4.8) were mixed in equal volume. After stirring for few minutes at room temperature the turbid reaction mixture become very clear and continued stirring for 2-3 days at room temperature. The reaction mixture was quenched and stored briefly by freezing at −20° C. After thawing, the crude mixture was precipitated from ice cold 2% $LiClO_4$ in acetone and centrifuged for 15 min at 4° C. The supernatant liquid was decanted off and washed further (twice) with ice-cold acetone. The crude mixture was evaporated to dryness under vacuum to obtain a white solid. The crude mixture was purified by reverse phase HPLC.

HPLC purification of Methylene-bis-deoxyadenosine-5'-monophosphate (dimer).

A small portion (~30 mg) of crude mixture was dissolved in ~500 μL of 0.1 M sodium phosphate buffer (pH 7.0) and purified via HPLC. A discontinuous linear gradient of acetonitrile in 0.1 M TEAA buffer (pH 7.5) was used: 0-1.0% for first 3 min, 1.0-8.0% for next 22 min, 8.0-95.0% for last 3 min. An elution rate of 3 ml/min was employed. The HPLC-purified fraction for Methylene-bis-AMP (retention time—25-26 min) was isolated and evaporated to dryness under vacuum.

Characterization of Methylene-Bis-dAMP (Dimer).

MALDI-HRMS m/z 707.1339 ([M+H]$^+$, $C_{21}H_{29}N_{10}O_{14}P_2$, Calc. 707.1340; $^1$H NMR ($D_2O$): δ 8.35 (s, 2H, H2), 8.20 (s, 2H, H8), 5.95-5.97 (d, 2H, J=5.6 Hz, H1'), 5.24 (s, 2H, N6-CH$_2$N6), 4.61 (t, 2H, J=5.3 Hz, H2'), 4.39-4.41 (m, 2H, H3'), 4.28-4.29 (m, 2H, H4'), 4.04-4.07 (m, 4H, H5').

Example 2

This example illustrates reversal of cross-linking chemistry of the dAMP dimer with catalysts.

Figure 2:
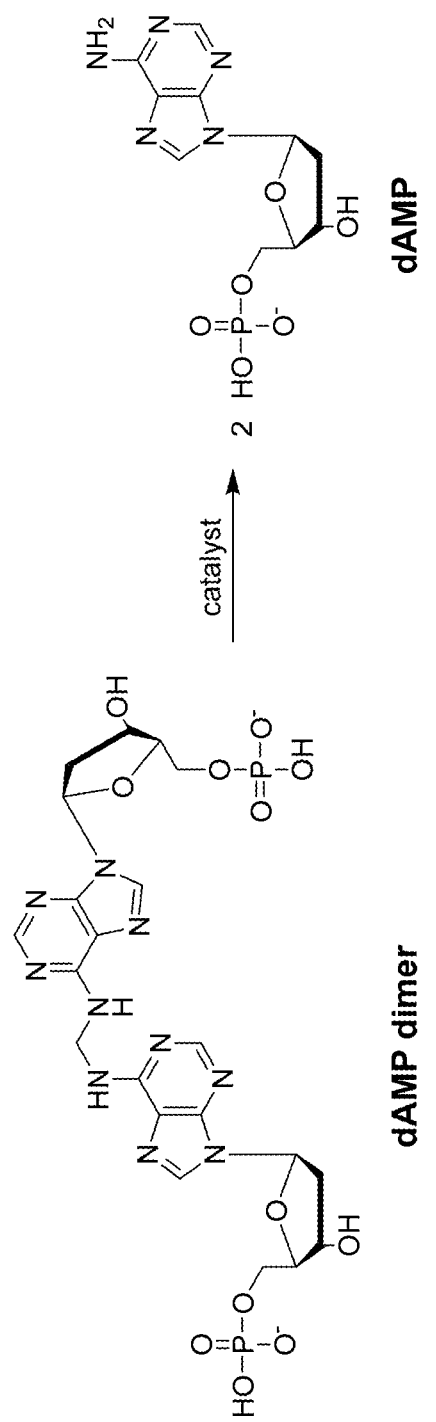
FIG. 2 illustrates an example of the "de-crosslinking" by catalysts of the present invention.
Figure 3:
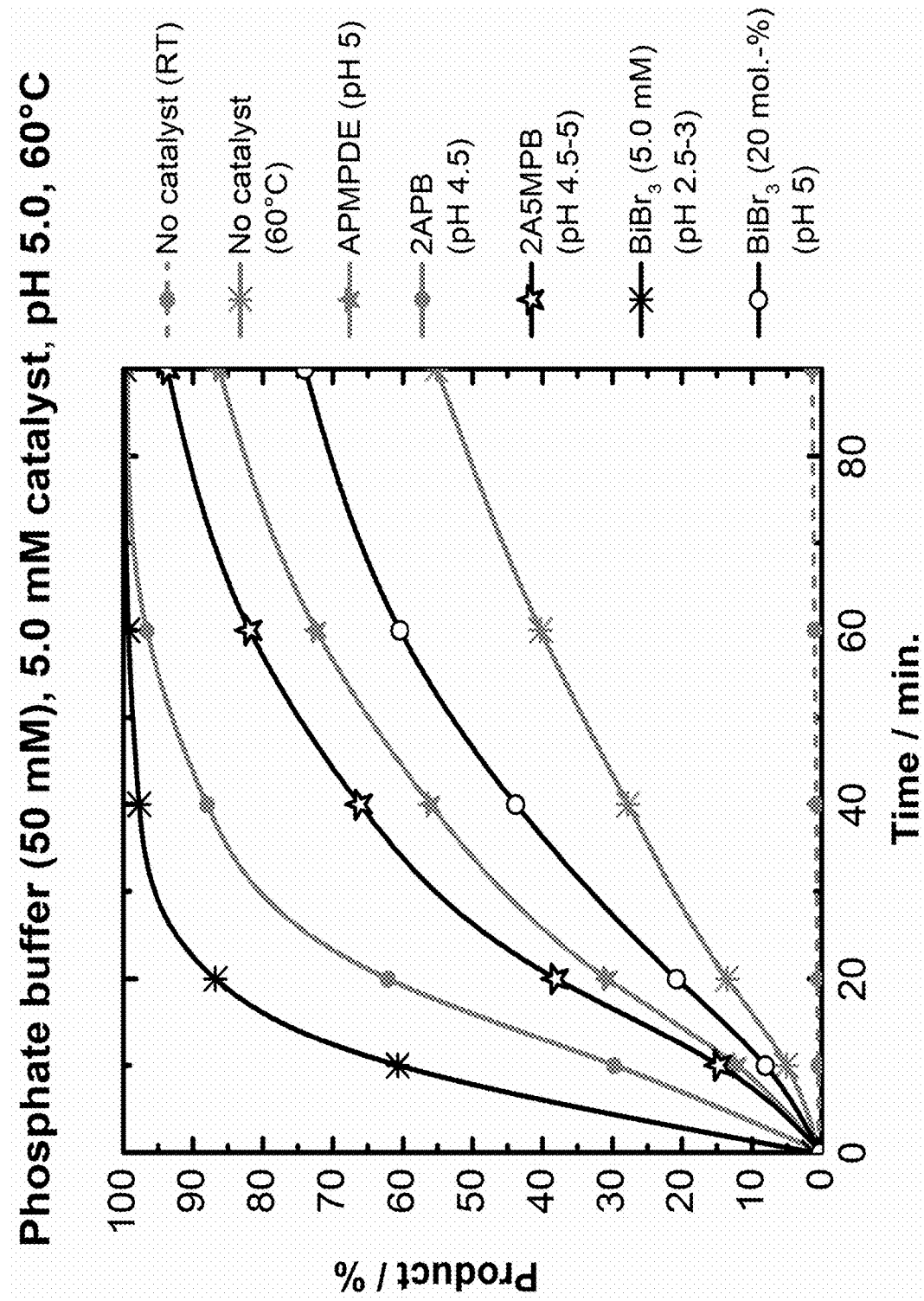
FIG. 3 illustrates the reversal of the dAMP dimer to the dAMP monomer under reaction conditions described in Example 2 in the absence of catalyst or in the presence of Compound 2 (2APB), Compound 3 (2A5MPB), Compound 6 (APMPDE) and Compound 7 ($BiBr_3$).

Reverse crosslinking of the methylene-bis-dAMP dimer (as shown in FIG. 2) were monitored by HPLC. Reactions were carried out on in 50 mM phosphate buffer, pH 5.0 at 60° C. dAMP dimer at 1.0 mM concentration was mixed with either no catalyst or with 5.0 mM concentration of Compounds 2, 3, 6, and 7. For each reaction mixture, an aliquot (10 μl) was taken at 10 minutes, 20 minutes, 40 minutes, 60 minutes and 90 minutes. FIG. 3 shows the results of this experiment and demonstrated that all the tested catalysts were able to reverse cross-linking (shown as % of dAMP produced) at rates that are much faster than when no catalyst was added.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for releasing one or more components within a formaldehyde cross-linked biological sample, the method comprising
    contacting the biological sample with a sufficient amount of a catalyst to release at least a portion of the one or more component, wherein the amount of catalyst is between 0.2 mM and 5.0 mM;
    and heating the biological sample and the catalyst at a temperature of 25° C. -60° C. for a period of at least ten minutes, thereby releasing the one or more component;
    wherein the catalyst is selected from the group consisting of a 2-aminophenylboronic acid, a cyclic phenylboronic acid ester, a phosphonic acid diethyl ester, and a bismuth salt.

2. The method of claim 1, wherein the biological sample is a tissue sample from an animal.

3. The method of claim 1, further comprising detecting the one or more component that has been released.

4. The method of claim 3, wherein the catalyst is substantially removed from the sample prior to the detecting step.

5. The method of claim 3, wherein the detecting step comprises quantifying the one or more component that has been released.

6. The method of claim 1, wherein the sample and catalyst are contacted at a pH range of between 4.5 and 8.0.

7. The method of claim 1, wherein the one or more component that has been released is a nucleic acid.

8. The method of claim 7, further comprising detecting the nucleic acid.

9. The method of claim 8, wherein the detecting step comprises amplifying the nucleic acid.

10. The method of claim 9, wherein the amplifying step comprises the polymerase chain reaction.

11. The method of claim 1, wherein the biological sample is embedded in paraffin prior to the contacting step.

12. The method of claim 1, wherein the catalyst is selected from the group consisting of (2-Amino-5-fluorophenyl) boronic acid, 2-Aminophenylboronic acid, (2-Amino-5-methylphenyl) boronic acid, 1,3-Dihydro-1-hydroxy-2,1-benzoxaborol-7-amine, 3,4-Dihydro-1-hydroxy-1H-2,1-benzoxaborin-7-amine, (Aminophenylmethyl) phosphonic acid diethyl ester, Bismuth (III) bromide, Bismuth (III), iodide, Bismuth (III) citrate and Bismuth (III) salicylate.

13. The method of claim 1, further comprising contacting the biological sample with a protease to degrade the protein in the biological sample.

14. A kit for improving the availability of one or more components of a formaldehyde cross-linked biological sample, the kit comprising,
a catalyst; and
a protease or a reagent or device for removal of the catalyst from a biological sample;
wherein the catalyst is selected from the group consisting of a 2-aminophenylboronic acid, a cyclic phenylboronic acid ester, a phosphonic acid diethyl ester, and a bismuth salt.

15. The kit of claim 14, wherein the kit comprises a reagent or device for removal of the catalyst from a biological sample.

16. The kit of claim 15, wherein the device is a column for purification of nucleic acids.

17. The kit of claim 14, wherein the kit comprises a protease.

18. The kit of claim 14, further comprising nucleotides and/or a thermostable polymerase.

19. The kit of claim 14 wherein the catalyst is selected from the group consisting of (2-Amino-5-fluorophenyl) boronic acid, 2-Aminophenyl boronic acid, (2-Amino-5-methylphenyl) boronic acid, 1,3-Dihydro-1-hydroxy-2,1-benzoxaborol-7-amine, 3,4-Dihydro-1-hydroxy-1H-2,1-benzoxaborin-7-amine, (Aminophenylmethyl) phosphonic acid diethyl ester, Bismuth (III) bromide, Bismuth (III), iodide, Bismuth (III) citrate and Bismuth (III) salicylate.

20. A reaction mixture comprising,
formaldehyde cross-linked biological sample; and
a sufficient amount of a catalyst to release at least a portion of the cross-linked component;
wherein the catalyst is selected from the group consisting of (2-Amino-5-fluorophenyl) boronic acid, 2-Aminophenyl boronic acid, (2-Amino-5-methylphenyl) boronic acid, 1,3-Dihydro-1-hydroxy-2,1-benzoxaborol-7-amine, 3,4-Dihydro-1-hydroxy-1H-2,1-benzoxaborin -7-amine, (Aminophenylmethyl) phosphonic acid diethyl ester, Bismuth (III) bromide, Bismuth (III), iodide, Bismuth (III) citrate and Bismuth (III) salicylate.

* * * * *